(12) United States Patent
Banas

(10) Patent No.: US 10,172,730 B2
(45) Date of Patent: Jan. 8, 2019

(54) STENTS WITH METALLIC COVERS AND METHODS OF MAKING SAME

(75) Inventor: Christopher E. Banas, Breckinridge, CO (US)

(73) Assignee: Vactronix Scientific, LLC, Fremont, CA (US)

( * ) Notice: Subject to any disclaimer, the term of this patent is extended or adjusted under 35 U.S.C. 154(b) by 1344 days.

(21) Appl. No.: 12/210,789

(22) Filed: Sep. 15, 2008

(65) Prior Publication Data

US 2009/0132022 A1     May 21, 2009

Related U.S. Application Data

(63) Continuation-in-part of application No. 10/289,974, filed on Nov. 6, 2002, now Pat. No. 7,491,226, which (Continued)

(51) Int. Cl.

| | | |
|---|---|---|
| A61F 2/06 | (2013.01) | |
| A61F 2/915 | (2013.01) | |
| A61F 2/07 | (2013.01) | |
| A61F 2/82 | (2013.01) | |
| A61F 2/91 | (2013.01) | |
| A61F 2/90 | (2013.01) | |

(52) U.S. Cl.
CPC ............... *A61F 2/915* (2013.01); *A61F 2/07* (2013.01); *A61F 2/82* (2013.01); *A61F 2/91* (2013.01); *A61F 2/90* (2013.01); *A61F 2002/072* (2013.01); *A61F 2002/075* (2013.01); *A61F 2002/91541* (2013.01); *A61F 2002/91558* (2013.01); *A61F 2220/005* (2013.01); *A61F 2220/0058* (2013.01)

(58) Field of Classification Search
CPC ...... A61F 2/07; A61F 2/91; A61F 2/90; A61F 2/82; A61F 2/915
USPC .......... 623/1.13, 1.18, 1.19, 1.32, 1.15, 1.11, 623/1.16, 1.38–1.49; 606/191–198; 427/2.24, 2.25
See application file for complete search history.

(56) References Cited

U.S. PATENT DOCUMENTS 4,337,665 A * 7/1982 Sato et al. .................. 73/766
4,510,182 A    4/1985 Cornils et al. ............. 427/162
(Continued)

FOREIGN PATENT DOCUMENTS

DE    1 452 370    8/1969    ............ B21C 37/15
EP    0 400 947    12/1990
(Continued)

OTHER PUBLICATIONS

Ametek Specialty Metal Products Online, "Sputtering targets high-quality thin film materials", www.ametek84.com/fd-sputtering.html, pp. 1-3.
(Continued)

*Primary Examiner* — Richard Louis
(74) *Attorney, Agent, or Firm* — David G. Rosenbaum; Benjamin D. Rotman; Rosenbaum IP, P.C.

(57) ABSTRACT

All metal stent grafts and covered stents having either a single structural supporting stent member with concentrically positioned graft members on the luminal and abluminal surfaces of the stent member or a single graft member with concentrically positioned structural supporting stent members on the luminal and abluminal surfaces of the graft member are provided.

33 Claims, 4 Drawing Sheets

Related U.S. Application Data is a continuation of application No. 09/532,164, filed on Mar. 20, 2000, now Pat. No. 6,537,310, which is a continuation-in-part of application No. 09/443,929, filed on Nov. 19, 1999, now Pat. No. 6,379,383, application No. 12/210,789, filed on Sep. 15, 2008, which is a continuation-in-part of application No. 10/936,883, filed on Sep. 9, 2004, now abandoned.

(56) References Cited

U.S. PATENT DOCUMENTS

| | | | | |
|---|---|---|---|---|
| 4,733,665 A | | 3/1988 | Palmaz | 128/343 |
| 4,739,762 A | | 4/1988 | Palmaz | 128/343 |
| 4,751,099 A | | 6/1988 | Niino et al. | 427/34 |
| 4,776,337 A | * | 10/1988 | Palmaz | 623/1.11 |
| 4,846,834 A | | 7/1989 | Von Recum et al. | 623/11 |
| 5,047,031 A | * | 9/1991 | Constantz | 606/77 |
| 5,049,251 A | | 9/1991 | Inoue | 204/192.12 |
| 5,061,914 A | | 10/1991 | Busch et al. | 337/140 |
| 5,084,151 A | | 1/1992 | Vallana et al. | 204/192.11 |
| 5,102,417 A | * | 4/1992 | Palmaz | A61F 2/91 |
| | | | | 604/103.05 |
| 5,133,732 A | | 7/1992 | Wiktor | 606/195 |
| 5,133,845 A | | 7/1992 | Vallana et al. | 204/192.15 |
| 5,158,750 A | | 10/1992 | Finicle | 422/102 |
| 5,207,706 A | * | 5/1993 | Menaker | A61L 27/306 |
| | | | | 604/266 |
| 5,242,710 A | | 9/1993 | Claar et al. | 427/248.1 |
| 5,277,933 A | | 1/1994 | Claar et al. | 427/248.1 |
| 5,329,514 A | | 7/1994 | Eguchi et al. | 369/126 |
| 5,330,500 A | * | 7/1994 | Song | 623/1.2 |
| 5,370,684 A | | 12/1994 | Vallana et al. | 623/1 |
| 5,376,463 A | | 12/1994 | Bak et al. | 428/547 |
| 5,387,247 A | | 2/1995 | Vallana et al. | 623/2 |
| 5,421,955 A | | 6/1995 | Lau et al. | 216/48 |
| 5,456,712 A | | 10/1995 | Maginot | 623/1 |
| 5,456,713 A | | 10/1995 | Chutter | 623/1 |
| 5,464,419 A | * | 11/1995 | Glastra | 606/194 |
| 5,477,864 A | | 12/1995 | Davidson | 128/772 |
| 5,514,154 A | | 5/1996 | Lau et al. | 623/1 |
| 5,522,881 A | * | 6/1996 | Lentz | A61F 2/07 |
| | | | | 606/191 |
| 5,522,882 A | | 6/1996 | Gaterud et al. | 623/1 |
| 5,540,820 A | | 7/1996 | Terakado et al. | 204/192.3 |
| 5,545,210 A | | 8/1996 | Hess et al. | 623/1 |
| 5,556,414 A | | 9/1996 | Turi | 606/198 |
| 5,569,295 A | | 10/1996 | Lam | 606/198 |
| 5,591,226 A | | 1/1997 | Trerotola et al. | 623/1 |
| 5,591,227 A | * | 1/1997 | Dinh et al. | 623/1.22 |
| 5,593,442 A | | 1/1997 | Klein | 623/12 |
| 5,603,721 A | | 2/1997 | Lau et al. | 606/195 |
| 5,605,714 A | | 2/1997 | Dearnaley et al. | 427/2.24 |
| 5,607,445 A | | 3/1997 | Summers | 606/198 |
| 5,607,463 A | * | 3/1997 | Schwartz | A61L 27/306 |
| | | | | 623/1.44 |
| 5,609,629 A | | 3/1997 | Fearnot et al. | 623/1 |
| 5,628,788 A | | 5/1997 | Pinchuk | 623/1 |
| 5,629,077 A | * | 5/1997 | Turnlund | A61F 2/82 |
| | | | | 156/308.2 |
| 5,630,840 A | | 5/1997 | Mayer | 623/1 |
| 5,632,779 A | * | 5/1997 | Davidson | 623/1.51 |
| 5,647,858 A | | 7/1997 | Davidson | 604/264 |
| 5,649,951 A | | 7/1997 | Davidson | 606/198 |
| 5,656,036 A | | 8/1997 | Palmaz | 623/12 |
| 5,665,115 A | | 9/1997 | Cragg | 623/1 |
| 5,667,523 A | * | 9/1997 | Bynon | A61F 2/07 |
| | | | | 606/194 |
| 5,683,448 A | | 11/1997 | Cragg | 623/1 |
| 5,683,453 A | | 11/1997 | Palmaz | 623/1 |
| 5,685,961 A | | 11/1997 | Pourrezaei et al. | 204/192.15 |
| 5,690,670 A | | 11/1997 | Davidson | 606/198 |
| 5,693,084 A | | 12/1997 | Chutter | 623/1 |
| 5,693,085 A | | 12/1997 | Buirge et al. | 623/1 |
| 5,695,517 A | | 12/1997 | Marin et al. | 606/198 |
| 5,702,419 A | | 12/1997 | Berry et al. | 606/198 |
| 5,713,947 A | * | 2/1998 | Davidson | A61B 17/72 |
| | | | | 623/1.51 |
| 5,723,219 A | | 3/1998 | Kolluri et al. | 428/411.1 |
| 5,725,573 A | | 3/1998 | Dearnaley et al. | 623/2 |
| 5,728,158 A | | 3/1998 | Lau et al. | 623/12 |
| 5,735,892 A | | 4/1998 | Myers et al. | 623/1 |
| 5,735,896 A | | 4/1998 | Amon et al. | 623/11 |
| 5,744,515 A | | 4/1998 | Clapper | 523/113 |
| 5,749,880 A | * | 5/1998 | Banas et al. | 606/198 |
| 5,755,775 A | | 5/1998 | Trerotola et al. | 623/1 |
| 5,765,418 A | | 6/1998 | Rosenberg | 72/47 |
| 5,769,884 A | * | 6/1998 | Solovay | A61F 2/07 |
| | | | | 606/194 |
| 5,772,864 A | | 6/1998 | Møller et al. | 205/73 |
| 5,776,161 A | | 7/1998 | Globerman | 606/194 |
| 5,780,807 A | | 7/1998 | Saunders | 219/121.71 |
| 5,782,908 A | | 7/1998 | Cahalan et al. | 623/1 |
| 5,782,910 A | | 7/1998 | Davidson | 623/3 |
| 5,788,558 A | | 8/1998 | Klein | 451/36 |
| 5,798,042 A | | 8/1998 | Chu et al. | 210/490 |
| 5,811,151 A | | 9/1998 | Hendriks et al. | 427/2.24 |
| 5,824,036 A | | 10/1998 | Lauterjung | 623/1 |
| 5,824,045 A | * | 10/1998 | Alt | A61F 2/91 |
| | | | | 205/184 |
| 5,824,049 A | | 10/1998 | Ragheb et al. | 623/1 |
| 5,824,054 A | | 10/1998 | Khosravi et al. | 623/1 |
| 5,824,056 A | | 10/1998 | Rosenberg | 623/1 |
| 5,824,058 A | | 10/1998 | Ravenscroft et al. | 623/1 |
| 5,840,009 A | | 11/1998 | Fischell et al. | 600/3 |
| 5,843,117 A | | 12/1998 | Alt et al. | 606/194 |
| 5,843,164 A | * | 12/1998 | Frantzen et al. | 623/1.16 |
| 5,843,289 A | | 12/1998 | Lee et al. | 204/192.3 |
| 5,849,206 A | | 12/1998 | Amon et al. | 216/63 |
| 5,855,600 A | | 1/1999 | Alt | 623/1 |
| 5,855,802 A | | 1/1999 | Acciai et al. | 216/8 |
| 5,855,955 A | | 1/1999 | Claar et al. | 427/248.1 |
| 5,858,556 A | * | 1/1999 | Eckert et al. | 428/586 |
| 5,866,113 A | | 2/1999 | Hendriks et al. | 424/78.17 |
| 5,868,782 A | | 2/1999 | Frantzen | 606/198 |
| 5,873,904 A | | 2/1999 | Ragheb et al. | 623/1 |
| 5,876,432 A | | 3/1999 | Lau et al. | 623/1 |
| 5,879,370 A | | 3/1999 | Fischell et al. | 606/198 |
| 5,891,507 A | | 4/1999 | Jayaraman | 427/2.25 |
| 5,895,406 A | | 4/1999 | Gray et al. | 606/198 |
| 5,897,911 A | | 4/1999 | Loeffler | 427/2.25 |
| 5,899,935 A | | 5/1999 | Ding | 623/1 |
| 5,902,332 A | | 5/1999 | Schatz | 623/1 |
| 5,907,893 A | | 6/1999 | Zadno-Azizi et al. | 29/6.1 |
| 5,913,896 A | | 6/1999 | Boyle et al. | 623/1 |
| 5,916,264 A | * | 6/1999 | Von Oepen | A61F 2/07 |
| | | | | 623/1.15 |
| 5,919,225 A | | 7/1999 | Lau et al. | 623/1 |
| 5,925,063 A | | 7/1999 | Khosravi | 606/200 |
| 5,925,075 A | | 7/1999 | Myers et al. | 623/1 |
| 5,928,279 A | | 7/1999 | Shannon et al. | 623/1 |
| 5,932,299 A | | 8/1999 | Katoot | 427/508 |
| 5,938,682 A | | 8/1999 | Hojeibane et al. | 606/198 |
| 5,938,697 A | | 8/1999 | Killion et al. | 623/1 |
| 5,945,153 A | | 8/1999 | Dearnaley | 427/2.12 |
| 5,951,881 A | | 9/1999 | Rogers et al. | 216/41 |
| 5,955,588 A | | 9/1999 | Tsang et al. | 536/21 |
| 5,962,138 A | | 10/1999 | Kolluri et al. | 428/411.1 |
| 5,968,091 A | | 10/1999 | Pinchuk et al. | 623/1 |
| 5,972,018 A | | 10/1999 | Israel et al. | 606/198 |
| 5,972,027 A | | 10/1999 | Johnson | 623/1 |
| 5,972,441 A | | 10/1999 | Campbell et al. | 428/34.1 |
| 5,984,905 A | | 11/1999 | Dearnaley | 604/265 |
| 6,001,123 A | | 12/1999 | Lau | 623/1 |
| 6,004,348 A | | 12/1999 | Banas et al. | 623/1 |
| 6,015,429 A | | 1/2000 | Lau et al. | 623/1 |
| 6,019,784 A | | 2/2000 | Hines | 623/1 |
| 6,022,370 A | | 2/2000 | Tower | 606/194 |
| 6,027,526 A | | 2/2000 | Limon et al. | 623/1 |
| 6,033,433 A | | 3/2000 | Ehr et al. | 623/1 |
| 6,036,725 A | * | 3/2000 | Avellanet | 623/1.13 |
| 6,039,755 A | | 3/2000 | Edwin et al. | 623/1 |
| 6,042,597 A | | 3/2000 | Kveen et al. | 606/198 |
| 6,042,605 A | | 3/2000 | Martin et al. | 623/1 |

(56) References Cited

U.S. PATENT DOCUMENTS

| | | | |
|---|---|---|---|
| 6,056,776 A | 5/2000 | Lau et al. ................... | 623/1.16 |
| 6,059,808 A | 5/2000 | Boussignac et al. ......... | 606/191 |
| 6,059,824 A * | 5/2000 | Taheri ......................... | 623/1.15 |
| 6,066,167 A | 5/2000 | Lau et al. ..................... | 623/1 |
| 6,066,168 A | 5/2000 | Lau et al. ..................... | 623/1.16 |
| 6,066,169 A | 5/2000 | McGuinness ................ | 623/1.16 |
| 6,071,305 A | 6/2000 | Brown et al. ................. | 623/1 |
| 6,086,773 A | 7/2000 | Dufresne et al. ............. | 216/8 |
| 6,096,175 A | 8/2000 | Roth ............................ | 204/192.15 |
| 6,106,642 A | 8/2000 | DiCarlo et al. ............... | 148/563 |
| 6,124,523 A | 9/2000 | Banas et al. .................. | 623/1.11 |
| 6,129,756 A | 10/2000 | Kugler et al. ................. | 623/1.27 |
| 6,139,573 A * | 10/2000 | Sogard et al. ................. | 623/1.13 |
| 6,143,022 A | 11/2000 | Shull et al. ................... | 623/1.13 |
| 6,156,064 A | 12/2000 | Chouinard .................... | 623/1.44 |
| 6,159,239 A | 12/2000 | Greenhalgh .................. | 623/1.13 |
| 6,162,244 A * | 12/2000 | Braun et al. .................. | 623/1.12 |
| 6,165,211 A | 12/2000 | Thompson .................... | 623/1.13 |
| 6,214,039 B1 | 4/2001 | Banas et al. .................. | 623/1.13 |
| 6,245,104 B1 * | 6/2001 | Alt ............................... | 427/2.25 |
| 6,251,132 B1 | 6/2001 | Ravenscroft et al. ......... | 623/1.11 |
| 6,264,598 B1 | 7/2001 | Armini ......................... | 600/1 |
| 6,264,684 B1 | 7/2001 | Banas et al. .................. | 623/1.13 |
| 6,264,689 B1 * | 7/2001 | Colgan et al. ................. | 623/1.22 |
| 6,306,164 B1 * | 10/2001 | Kujawski ...................... | 623/1.35 |
| 6,312,463 B1 | 11/2001 | Rourke et al. ................ | 623/1.39 |
| 6,322,585 B1 | 11/2001 | Khosravi et al. ............. | 623/1.11 |
| 6,334,868 B1 * | 1/2002 | Ham ............................ | A61F 2/07 |
| | | | 623/1.13 |
| 6,344,053 B1 | 2/2002 | Boneau ......................... | 623/1.11 |
| 6,344,054 B1 | 2/2002 | Parodi .......................... | 623/1.13 |
| 6,346,119 B1 | 2/2002 | Kuwahara et al. ............ | 623/1.13 |
| 6,348,066 B1 | 2/2002 | Pinchuk et al. ............... | 623/1.16 |
| 6,352,553 B1 | 3/2002 | van der Burg et al. ....... | 623/1.23 |
| 6,355,058 B1 | 3/2002 | Pacetti et al. ................. | 623/1.15 |
| 6,361,637 B2 | 3/2002 | Martin et al. ................. | 156/187 |
| 6,377,721 B1 * | 4/2002 | Walt et al. .................... | 385/12 |
| 6,379,383 B1 | 4/2002 | Palmaz et al. ................ | 623/1.49 |
| 6,383,214 B1 | 5/2002 | Banas et al. .................. | 623/1.14 |
| 6,387,121 B1 | 5/2002 | Alt ............................... | 623/1.15 |
| 6,391,052 B2 | 5/2002 | Buirge et al. ................. | 623/1.47 |
| 6,398,802 B1 | 6/2002 | Yee .............................. | 623/1.13 |
| 6,416,535 B1 | 7/2002 | Lazarus ........................ | 623/1.11 |
| 6,428,569 B1 | 8/2002 | Brown .......................... | 623/1.15 |
| 6,451,047 B2 | 9/2002 | McCrea et al. ............... | 623/1.13 |
| 6,475,232 B1 | 11/2002 | Babbs et al. .................. | 623/1.13 |
| 6,488,701 B1 | 12/2002 | Nolting et al. ................ | 623/1.13 |
| 6,500,203 B1 | 12/2002 | Thompson et al. ........... | 623/1.13 |
| 6,520,986 B2 | 2/2003 | Martin et al. ................. | 623/1.13 |
| 6,537,310 B1 | 3/2003 | Palmaz et al. ................ | 623/1.13 |
| 6,730,119 B1 * | 5/2004 | Smalling ...................... | 623/1.35 |
| 7,491,226 B2 * | 2/2009 | Palmaz et al. ................ | 623/1.13 |
| 7,641,680 B2 * | 1/2010 | Palmaz et al. ................ | 623/1.13 |
| 7,704,274 B2 * | 4/2010 | Boyle et al. .................. | 623/1.13 |
| 7,717,949 B2 * | 5/2010 | Dorn ............................ | 623/1.11 |
| 2001/0034550 A1 * | 10/2001 | Buirge et al. ................. | 623/1.47 |
| 2001/0039449 A1 | 11/2001 | Johnson et al. ............... | 623/1.19 |
| 2002/0123789 A1 * | 9/2002 | Francis ......................... | A61F 2/07 |
| | | | 623/1.13 |
| 2003/0225448 A1 * | 12/2003 | Gerberding ................... | A61F 2/91 |
| | | | 623/1.15 |
| 2004/0054399 A1 | 3/2004 | Roth ............................. | 623/1.16 |
| 2008/0034550 A1 * | 2/2008 | Chang et al. ................. | 16/367 |

FOREIGN PATENT DOCUMENTS

| | | | | |
|---|---|---|---|---|
| EP | 0 442 303 | 8/1991 | ............. | C23C 16/26 |
| JP | 51055724 | 5/1976 | | |
| JP | 61-88135 | 5/1986 | ............. | G01N 27/30 |
| JP | 11/267462 | 10/1999 | ............. | B01D 59/34 |
| WO | WO94/25081 | 11/1994 | ............. | A61L 33/00 |
| WO | WO97/07257 | 2/1997 | ............. | C23C 14/00 |
| WO | WO97/44692 | 11/1997 | ............. | G02B 6/16 |
| WO | WO97/46268 | 12/1997 | ............. | A61L 29/00 |
| WO | WO98/13537 | 4/1998 | ............. | C25D 1/00 |
| WO | WO98/45506 | 10/1998 | ............. | C25D 7/04 |
| WO | WO99/23977 | 5/1999 | ............. | A61F 2/06 |
| WO | WO00/54704 | 9/2000 | ............. | A61F 2/06 |
| WO | WO01/53559 | 7/2001 | ............. | A61F 2/06 |
| WO | WO01/55473 | 8/2001 | ............. | C23C 14/00 |
| WO | WO01/56502 | 8/2001 | ............. | A61F 2/06 |
| WO | WO02/04197 | 1/2002 | ............. | B32B 1/08 |

OTHER PUBLICATIONS

AVS 46th International Symposium, Paper BI-WeM5, "Biocompatibility of cardiac cells on silane-modified surfaces" (Oct. 27, 1999).
AVS 46th International Symposium, Paper BI-WeM7, "Biofunctionalization of surfaces with peptide amphilphiles", (Oct. 27, 1999).
AVS 46th International Symposium, Paper BI-WeM9, "Plasma copolymer surfaces for cell culture" (Oct. 27, 1999).
AVS 46th International Symposium, Paper BI-FrM2, "Plasma copolymer surfaces for the controlled adsorption of common proteins", (Oct. 29, 1999).
AVS 46th International Symposium, Paper BI-FrM10, "Biofilm—titanium chemistry of adhesion using X-ray photoelectron spectroscopy" (Oct. 29, 1999).
AVS 46th International Symposium, Paper BI-FrM10, "Nanoscale patterning of gold for attachment of supported lipid bilayers" (Oct. 29, 1999).
Banning, L, et al., "The experimental use of steel mesh tubes for the replacement of arterial segments," *Presented at the Third Scientific Meeting of the North American Chapter of the International Society of Angiology*, Atlantic City, NJ, pp. 69-75 (Jun. 4, 1955).
Buchaillot, L., et al., "Constitutive parts of a shape memory alloy titanium-nickel thin film catheter," *Proceedings of the Second International Conference on Shape Memory and Superelastic Technologies Asilomar Conference Center*, Pacific Grove, California, USA, pp. 183-188 (1997).
Busch, J.D., et al., "Shape memory properties in Ni—Ti sputter-deposited film," *J Appl. Phys*, 68:12, pp. 6224-6226 (Dec. 15, 1990).
Cejna, Manfred, et al., "Primary implantation of polyester-covered stent-grafts for transjugular introhepatic portosystemic stent shunts (TIPSS): A pilot study," *Cardiovasc Intervent Radiol*, 22: pp. 305-310 (1999).
Chu, J.P. et al., (Abstract): "Deposition and characterization of TiNi-base thin films by sputtering" *Materials Science and Engineering*, vol. A277, pp. 11-17 (2000).
Curtis, et al., "Reactions of biological cells to nanostructures," AVS 46th International Symposium, Paper BI-WeM2 (Oct. 27, 1999).
Davies, P.F., et al., "Endothelial cell adhesion in real time. Measurements in vitro by tandem scanning confocal image analysis," *J. Clin Invest*, 91: 6, pp. 2640-2652 (Jun. 1991).
Davies, P.F., et al., "Quantitative studies of endothelial cell adhesion. Directional remodeling of focal adhesion sites in response to flow forces," *J. Clin Invest.*, 93: 5, pp. 2031-2038 (May 1994).
Daw, R. et al., "Endothelial cell organization on micropatterned protein surfaces," AVS 47th International Symposium, Paper No. BI-WeP21 (Oct. 4, 2000).
Edelman, E., et al., "Gold-coated NIR stents in porcine coronary arteries", *Circulation*, pp. 429-434 (Jan. 23, 2001).
Ensinger, W., "The influence of ion irradiation during film growth on the chemical stability of film/substrate systems," *Surface and Coatings Technology*, 80: pp. 35-48 (1996).
Fancey, K.S., et al., (Abstract) "Relative importance of bombardment energy and intensity in ion plating," *Journal of VacuumScience & Technology A: Vacuum, Surfaces and Films*, 13:2, pp. 428-435 (Abstract view) Mar. 1995.
Gisser, K., et al., (Abstract) "Oriented nickel-titanium shape memory alloy films prepared by annealing during deposition", *Applied Physics Letters*, 61:14, pp. 1632-1634.
Goldberg, F., et al., "The effects of ion irradiation on NiTi shape memory alloy thin films," *Proceedings of the Second International Conference on Shape Memory and Superelastic Technologies Asilomar Conference Center*, Pacific Grove, California, USA, pp. 177-182 (1997).

(56) References Cited

OTHER PUBLICATIONS

Gordon, et al., (Abstract): "Liquid sources for chemical vapor deposition of group 6 metals and Metal nitrides,", www.techtransfer.harvard.edu/cgi-bin/TALSearch.cgi?full_report=1&case=3, Case No. 1709.

Gutensohn, Kai, M.D., "Flow Cytometric Investigation", http://www.phytis.com/stent6.htm, pp. 1-3.

Haskal, Z.J., et al., (Abstract): "Porous and nonporous polycarbonate urethane stent-grafts for TIPS formation: biologic responses," *J. Vasc. Interv. Radiol*, 10:9, pp. 1255-1263 (Oct. 1999).

Haskal, Z.J., "Improved patency of transjugular intrahepatic portosystemic shunts in humans: Creation and revision with PTFE stent-grafts" *Radiology*, 213:3, pp. 759-766 (Dec. 1999).

Houston, J.E., "The nanomechanical properties of thin films," *AVS 47th International Symposium*, Paper No. TF-TuA1 (Oct. 3, 2000).

IBM, "Multicomponent film deposition by target biasing," *IBM Technical Disclosure Bulletin*, pp. 1-2 (Jul. 1980).

IEM, "Expertise concerning the implementation of the Phytis Diamond as Stent performed at the Institute for Experimental Medicine (IEM)," http://www.phytis.com/stent9,htm, pp. 1.

Inoue, K., et al., "Aortic arch reconstruction by transluminally placed endovascular branched stent graft," *Circulation*, pp. II316-II321 (Nov. 9, 1999).

Ishida, A., et al., "Microstructure of Ti-Rich Ti—Ni thin films," *Proceedings of the Second International Conference on Shape Memory and Superelastic Technologies Asilomar Conference Center*, Pacific Grove, California, USA, pp. 161-166 (1997).

Jardine, A. Peter, "Vacuum conditions for sputtering thin film TiNi," (Abstract view), *Journal of Vacuum Science and Technology, JVST A Online*, pp. 1-2.

Johnson, A.D., et al., "Recent progress in the application of thin film shape memory alloys," *Proceedings of the First International Conference on Shape Memory and Superelastic Technologies Asilomar Conference Center*, Pacific Grove, California, USA, pp. 299-310 (1994).

Johnson, A.D., et al., "Applications of shape-memory alloy thin films," *Proceedings of the Second International Conference on Shape Memory and Superelastic Technologies Asilomar Conference Center*, Pacific Grove, California, USA, pp. 1-12 (1997).

Johnson, et al., "Progress in thin film shape memory microactuators," by Johnson, et al., www.sma-mems.com/recent.htm (Overview), pp. 1-5.

Kalman, Peter G., M.D. "Stent-graft repair for abdominal aortic aneurysm," *CMAJ*, 161:9, pp. 1133.

Kusano, E., et al., "Anomalous plastic and elastic behaviors of sputter-deposited TiN with 10 or 20 inserted thin Al layers evaluated by nanoindentation," *AVS 47th International Symposium*, Paper No. TF-TuA3 (Oct. 3, 2000).

Mattox, D., "A concise history of vacuum coating technology, Part 2: 1940 to 1975," www.svc.org/Historyof_Vac2.html, pp. 1-15.

Mrksich, M., "Model surfaces for studying and controlling the adhesion of cells," *AVS 47th International Symposium*, Invited Paper No. BI+EL-TuA1 (Oct. 3, 2000).

Nishikawa, T., et al., "Tissue formation of hepatocytes on microporous films of polylactide," *AVS 47th International Symposium*, Paper No. BI+EL-TuA10 (Oct. 3, 2000).

Phytis, L.D.A. Home Page Information, http://www.phytis.com/continent/htm, pp. 1-15.

Pingshan, Q., et al., The effect of HCD technological factors on the NiTi SMA film thickness, *Proceedings of the Second International Conference on Shape Memory and Superelastic Technologies Asilomar Conference Center*, Pacific Grove, California, USA, pp. 173-176 (1997).

Quandt, E., et al., "Sputter-deposition of TiNi, TiNiPd and TiPd films displaying the two-way shape-memory effect," *Sensors and Actuators*, A53, pp. 434-439 (1996).

Serruys, P.W., et al., "Handbook of coronary stents," Third Ed. (2000).

Singh, J., "Multilayer ceramic/metallic coatings by ion beam-assisted, electron beam physical vapor (EB-PVD) deposition", *Penn State Appled Research Laboratory*, pp. 1-4 (1997).

Stolf, N.A., et al., (Abstract): "Self-expanding endovascular stent-graft implant for treatment of descending aortic diseases", *J. Card. Surg.*, 14:1, pp. 9-15 (Jan.-Feb. 1999).

Sutherland, D.S., et al., "Cell response to chemically and topographically modified surfaces," *AVS 47th International Symposium*, Paper No. BI+EL-TuA3 (Oct. 3, 2000).

TiNi Alloy Compay (online), "Thin film shape memory alloy microactuators", pp. 1-2.

Uhrmeister, P, et al., (Abstract): "Stents for the treatment of aortic aneurysms. Review of devices, technique and results", *Thromb Haemost*, 82(Suppl):1, pp. 171-175 (Sep. 1999).

Vroman, L., "The importance of surfaces in contact phase reactions," *Seminars of Thrombosis and Hemostasis*, 13:1, pp. 79-85 (1987).

Walker, J.A., et al., "Thin-film processing of TiNi shape memory alloy," *Sensors and Actuators*, A21-A23, pp. 243-246 (1990).

Weixin, H., et al., "The characteristics of NiTi HCD-deposited SMA films," *Proceedings of the Second International Conference on Shape Memory and Superelastic Technologies Asilomar Conference Center*, Pacific Grove, California, USA, pp. 167-172 (1997).

Ye, et al., "Bioresorbable microporous stents deliver recombinant adenovirus gene transfer ventors to the arterial wall," *Annals of Biomedical Engineering*, 26: pp. 298-408 (1998).

Zheng, H., et al., (Abstract): "Clinical experience with a new biocompatible phosphorylcholine-coated coronary stent," *J. Invasive Cardiol*, 11:10, pp. 608-614 (Oct. 1999).

"Adhesion of bovine serus albumin on coated DLC (diamond-like) and uncoated ($SiO_2$ / $TiO_2$) sensor chips," http://wwwphytis.com/stent4.htm, pp. 1-2.

"Amorphous carbon and C:N thin films," http://www.glue.umd.edu/~astan/avs01.htm.

"Benefits from diamond-like coated stainless steel stents", http://www.phytis.com/stents0.htm, pp. 1-2.

"Directions for use, Diamond AS® stent", www.phytis.com/direcuse.htm, pp. 1-8.

"Fabrication of small-scale coils and bands as photomasks on optical fibers for generation of in-fiber gratings, electromagnets as Micro-NMR coils, microtransformers, and intra-vascular stents," www.techtransfer.harvard.edu/cgi-bin/TALSearch.cgi?full_report=1&case=72, Case No. 1263.

"Focused ion beam nonafabrication," http://www.glue.umd.edu/~astan/avs04.htm.

"Invulnerability and resistance of DLC-coating," http://www.phytis.com/stent3.htm, pp. 1-3.

"Material in use and its biocompatibility," http://www.phytis.com/stent5.htm, pp. 1-2.

"Photolithographic fine patterning of difficult-to-etch-metals," http://www.nasatech.com/Briefs/Mar02/LEW17079.html, pp. 1-4.

"Pre-clinical and clinical evaluation," http://www.phytis.com/stent2.htm, pp. 1B2.

"Risk analysis of stents with a diamond-like coated surface for use in prosthetic implants," http://www.phytis.com/risk.htm, pp. 1-6.

"Stents: Literature," http://www.phytis.com/liter.htm, pp. 1-8.

"The new Phytis stent," http://www.phytis.com/stent1.htm, pp. 1-2.

\* cited by examiner

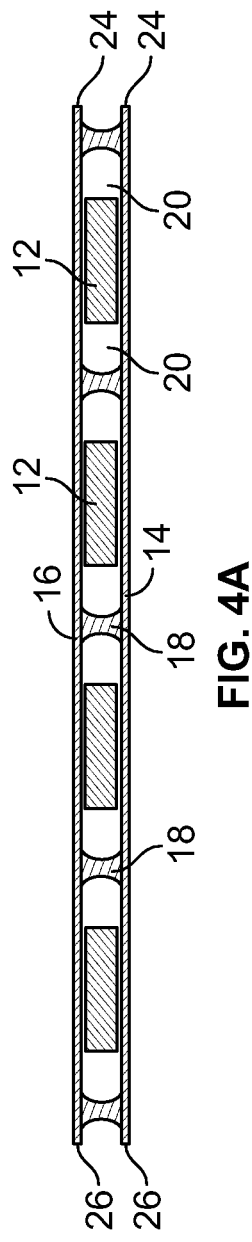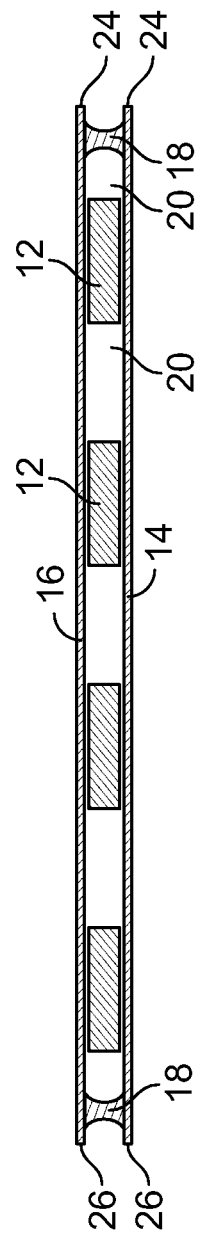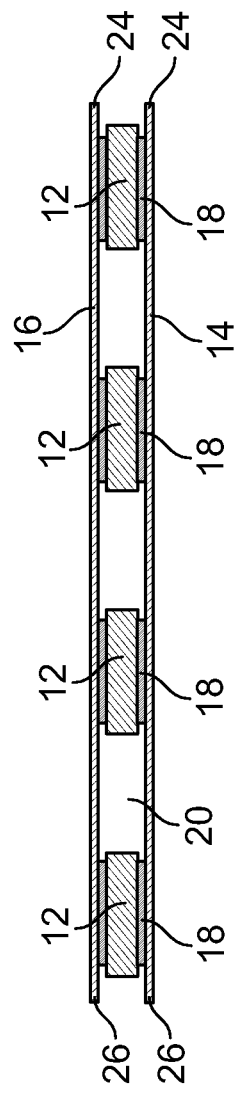

STENTS WITH METALLIC COVERS AND METHODS OF MAKING SAME

CROSS-REFERENCE TO RELATED INVENTIONS

This application is a continuation-in-part of U.S. patent application Ser. No. 10/936,883, filed on Sep. 9, 2004. This application is also a continuation-in-part of U.S. patent application Ser. No. 10/289,974, filed on Nov. 6, 2002, which is a continuation of U.S. patent application Ser. No. 09/532,164, filed on Mar. 20, 2000, now U.S. Pat. No. 6,537,310, which is a continuation-in-part of U.S. patent application Ser. No. 09/443,929, filed on Nov. 19, 1999, now U.S. Pat. No. 6,379,383, each of which is hereby incorporated by reference in its entirety.

BACKGROUND OF THE INVENTION

The present invention pertains generally to the field of medical devices intended to maintain patency of anatomical passageways, such as those found in the cardiovascular, lymphatic, endocrine, renal, gastrointestinal and/or reproductive systems of mammals. More particularly, the present invention relates to stents, stent-grafts and covered stents that are designed for endoluminal delivery using a delivery catheter and minimally invasive surgical techniques. The present invention generally comprises stent-graft or covered stent type devices that are fabricated entirely of biocompatible metals or of biocompatible materials that exhibit biological response and material characteristics substantially the same as biocompatible metals, such as, for example, composite materials. For purposes of the present application, the terms "stent-graft" and "covered stent" are used interchangeably.

Conventional endoluminal stents and stent-grafts are frequently used in conjunction with a procedure which dilitates an occluded, obstructed or diseased anatomical passageway to provide structural support and maintain the patency of the anatomical passageway. An example of this is the post-angioplasty use of intravascular stents to provide a structural support for a blood vessel and reduce the incidence of restenosis. Principal, but non-limiting, examples of the present invention include endovascular stents which are introduced to a site of disease or trauma within the body's vasculature from an introductory location remote from the disease or trauma site using an introductory catheter, passed through the vasculature communicating between the remote introductory location and the disease or trauma site, and released from the introductory catheter at the disease or trauma site to maintain patency of the blood vessel at the site of disease or trauma. Stent-grafts are delivered and deployed under similar circumstances and are utilized to maintain patency of an anatomic passageway, for example, by reducing restenosis following angioplasty, or when used to exclude an aneurysm, such as in aortic aneurysm exclusion applications.

While the use of endoluminal stents has successfully decreased the rate of restenosis in angioplasty patients, it has been found that a significant restenosis rate continues to exist even with the use of endoluminal stents. It is generally believed that the post-stenting restenosis rate is due, in major part, to the non-regrowth of a healthy endothelial layer over the stent and the incidence of smooth muscle cell-related neointimal growth on the luminal surfaces of the stent. Injury to the endothelium, the natural nonthrombogenic lining of the arterial lumen, is a significant factor contributing to restenosis at the situs of a stent. Endothelial loss exposes thrombogenic arterial wall proteins, which, along with the generally thrombogenic nature of many prosthetic materials, such as stainless steel, titanium, tantalum, nitinol, etc., customarily used in manufacturing stents, initiates platelet deposition and activation of the coagulation cascade, which results in thrombus formation, ranging from partial covering of the luminal surface of the stent to an occlusive thrombus. Additionally, endothelial loss at the site of the stent has been implicated in the development of neointimal hyperplasia at the stent situs. Accordingly, rapid re-endothelialization of the arterial wall with concomitant endothelialization of the body fluid or blood contacting surfaces of the implanted device is important for maintaining vasculature patency and preventing low-flow thrombosis.

At present, most endoluminal stents are manufactured of either stainless steel or nickel-titanium alloy, both of which are known to be thrombogenic. In order to reduce the thrombogenicity of the stainless steel and to maintain sufficient dimensional profiles for catheter delivery, most stents minimize the metal surface area that contacts blood in order to minimize thrombus formation after implantation. Thus, in order to reduce the thrombogenic response to stent implantation, as well as to reduce the formation of neointimal hyperplasia, it would be advantageous to increase the rate at which endothelial cells form endothelium proximal and distal to the stent situs, migrate onto, and provide endothelial coverage of the luminal surface of the stent which is in contact with blood flow through the vasculature.

Stent-grafts are essentially endoluminal stents with a discrete covering on either or both of the luminal and abluminal surfaces of the stent that occludes the open spaces, or interstices, between adjacent structural members of the endoluminal stent. It is known in the art to fabricate stent-grafts by covering the stent with endogenous vein or a synthetic material, such as woven polyester known as DACRON®, or with expanded polytetrafluoroethylene. Additionally, it is known in the art to cover the stent with a biological material, such as a xenograft or collagen. A primary purpose for covering stents is to reduce the thrombogenic effect of the stent material and reduce particulate extrusion through interstices of the stent and into the bloodstream. Conventional graft materials have not proven to be a complete solution to enhancing the healing response of conventional stents.

Heretofore, the art has not provided a stent-graft device in which a structural component, such as a stent, and a graft component are each fabricated of biocompatible metals or of biocompatible materials which exhibit in vivo biological and mechanical responses substantially the same as biocompatible metals (hereinafter synonymously referred to as "pseudometals" or "pseudometallic materials").

SUMMARY OF THE INVENTION

In one aspect, the present invention provides a stent-graft type device fabricated entirely of biocompatible metals and/or pseudometallic materials. That is, the inventive stent-graft type device comprises generally of a structural component, e.g., a stent, a plurality of stents, or a plurality of support structures, and a covering component, e.g., a graft, each of which is formed of a metal or pseudometal. For ease of reference, the structural component will be termed a "stent", while the covering component will similarly be termed a "graft". Those of ordinary skill in the art will appreciate, however, that the terms "structural component"

and "covering component" have broader meaning and encompass a wide variety of structures other than stents or grafts.

The stent may comprise of any type of structural member and is preferably generally tubular in configuration, and has an inner or luminal wall and an outer or abluminal wall and a central lumen passing along the longitudinal axis of the stent. The stent may be comprised of a wide variety of geometric configurations and constructions, as are known in the art. For example, the stent may assume a balloon expandable slotted configuration of U.S. Pat. No. 4,733,665, 4,739,762, 4,776,337 or 5,102,417, or the stent may be configured as a plurality of self-expanding interwoven wire members, or it may assume any of the wall geometries disclosed in Serruys, P. W., Kutryk, M. J. B., *Handbook of Coronary Stents*, $3^{rd}$ Ed. (2000). Each of the stent designs, stent materials, stent material characteristics, e.g., balloon expandable, self-expanding by spring tension of the material, self-expanding by shape memory properties of the stent material, or self-expanding by superelastic properties of the stent material are well known to one of ordinary skill in the art and may be used with the stent-graft of the present invention.

The covering component, or the graft of the present invention may be employed on either or both of the luminal wall and/or the abluminal wall of the stent, and may cover all or a portion of either or both of the luminal and/or abluminal walls of the stent. The graft may be formed as a planar film of material that is applied to the stent by wrapping about the stent or formed into a tubular structure and coupled to the stent. Alternatively the graft may be formed as an integral tubular member that is coupled to the stent. The graft may also be fashioned as at least two graft members, with a first graft member covering a luminal wall surface of the stent and a second graft member covering an abluminal wall surface of the stent. Alternatively, the graft may be formed as a single member that covers both a luminal wall surface and an abluminal wall surface of the stent and is everted over either or both ends of the stent. Further, the graft member may be joined to the stent, or where a graft covers both the luminal and abluminal wall surfaces of the stent, the graft may be joined to an opposing graft surface through interstices in the stent. The juncture between the graft and the stent or between the graft and the graft through the stent may be accomplished by chemical, mechanical or thermal means such as by welding, adhesion using biocompatible adhesives, interference fits, interlocking or interfacing couplings, such as an interfacing detent and trough combination, or such other methods of joining or coupling a metallic and pseudometallic material to itself or such materials to one another as are known in the art. Where an interfacing detent-trough combination is employed as a coupling, it may be a direct interface or it may serve to lock the graft material into a fixed position relative to the structural support members. Further, in order to minimize percent strain resulting from the coupling of a trough and detent, it is desirable that the detent and trough have radiused surfaces.

The structural support component and the covering component are preferably fabricated entirely of self-supporting films made of biocompatible metals or biocompatible pseudometals. The metal films may either be single layer metal films or plural layer films. The terms "metal film," "thin metallic film" and "metal thin film" are used in this application synonymously to refer to single or plural layer films fabricated of biocompatible metals or biocompatible pseudometals having thicknesses greater than 0 μm and less than about 125 μm. When used as the structural support component, the thin metallic film preferably has a thickness greater than about 25 μm and when used as the covering component, the thin metallic film preferably has a thickness between about 0.11 m and about 25 μm and most preferably between about 0.1 μm and about 10 μm.

There are generally two embodiments of the inventive stent-graft. A first embodiment consists of a stent covered by graft material on each of the luminal and abluminal wall surfaces of the stent. A second embodiment consists of first and second stent members concentrically positioned coaxial with one another, with at least one graft member concentrically positioned intermediate the first and second stent members. In this second embodiment, the at least one graft member may further encapsulate one or both of the first and second stent members.

In accordance with an inventive method for making the inventive stent-graft, at least one discrete graft member may be conjoined with a plurality of structural members, such as a stent, by joining or coupling the graft member to regions of the structural members. The joined regions may be at a proximal and/or a distal end of the device, or may be at intermediate regions along the longitudinal and circumferential axes of the device. Alternatively, where the graft member or members cover both the luminal and abluminal wall surfaces of the structural members, the graft member or members may be mechanically joined to one another through interstices formed between adjacent pairs of structural members. An alternative method for making the inventive stent-graft includes employing vacuum deposition methodologies, such as those employed in the microelectronics fabrication arts. For example, sputtering, physical vapor deposition, ion beam-assisted evaporative deposition or the like, may be used to create either or both of the graft and the stent components of the inventive stent-graft device. In ion beam-assisted evaporative deposition, it is preferable to employ dual and simultaneous thermal electron beam evaporation with simultaneous ion bombardment of the material being deposited using an inert gas, such as argon, xenon, nitrogen or neon. Bombardment with inert gas ions during deposition serves to reduce void content by increasing the atomic packing density in the deposited material. The reduced void content in the deposited material allows the mechanical properties of that deposited material to be similar to the bulk material properties. Deposition rates up to 20 nm/sec are achievable using ion beam-assisted evaporative deposition techniques.

When sputtering techniques are employed, a 200-micron thick stainless steel film may be deposited within about four hours of deposition time. Thinner films may be achieved by using shorter deposition times. With the sputtering technique, it is preferable to employ a cylindrical sputtering target, a single circumferential source that concentrically surrounds the substrate that is held in a coaxial position within the source.

During deposition, various deposition process parameters, including, without limitation, target composition, target temperature, chamber pressure, deposition pressure, deposition rate, target configuration, target-to-source distance, bias or partial pressure of the process gases are controlled to optimize deposition of the desired species onto the substrate. As is known in the microelectronic fabrication, nano-fabrication and vacuum coating arts, both the reactive and non-reactive gases are controlled and the inert or non-reactive gaseous species introduced into the deposition chamber is typically argon. The substrate may be either stationary or moveable; either rotated about its longitudinal axis, moved in an X-Y plane, planatarily or rotationally moved within the deposition chamber to facilitate deposition or patterning of the deposited material onto the substrate. The deposited material may be deposited either as a uniform solid film onto the substrate, or patterned by (a) imparting either a positive or negative pattern onto the substrate, such as by etching or photolithography techniques applied to the substrate surface to create a positive or negative image of the desired pattern or (b) using a mask or set of masks which are either stationary or moveable relative to the substrate to define the pattern applied to the substrate. Patterning may be employed to achieve complex finished geometries of the resultant structural supports, web-regions or graft, both in the context of spatial orientation of patterns of regions of relative thickness and thinness, such as by varying the thickness of the film over its length to impart different mechanical characteristics under different delivery, deployment or in vivo environmental conditions.

The device may be removed from the substrate after device formation by any of a variety of methods. For example, the substrate may be removed by chemical means, such as etching or dissolution, by ablation, by machining or by ultrasonic energy. Alternatively, a sacrificial layer of a material, such as carbon, aluminum or organic based materials, such as photoresists, may be deposited intermediate the substrate and the stent and the sacrificial layer removed by melting, chemical means, ablation, machining or other suitable means to free the stent from the substrate.

Optionally, the resulting device may then be subjected to post-deposition processing to modify the crystalline structure, such as by annealing, or to modify the surface topography, such as by etching to expose a heterogeneous surface of the device.

Alternate deposition processes which may be employed to form the stent in accordance with the present invention are cathodic arc, laser ablation, and direct ion beam deposition. As known in the metal fabrication arts, the crystalline structure of the deposited film affects the mechanical properties of the deposited film. These mechanical properties of the deposited film may be modified by post-process treatment, such as by, for example, annealing.

Materials to make the inventive graft, stent-graft and web-stent are chosen for their biocompatibility, mechanical properties, i.e., tensile strength, yield strength, and their ease of deposition and include, without limitation, the following: elemental titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, nitinol, and stainless steel.

The inventive stent-graft type device of the present invention is formed entirely of metal or pseudometallic material that exhibits improved endothelialization and healing response as compared to that associated with using conventional synthetic polymeric graft materials.

BRIEF DESCRIPTION OF THE DRAWINGS

FIG. 4A is a cross-sectional view of a second embodiment of the stent-graft of the present invention.

FIG. 4B is a cross-sectional view of a variation of a second embodiment of the stent-graft of the present invention.

FIG. 4C is a cross-sectional view of another variation of a second embodiment of the stent-graft of the present invention.

DETAILED DESCRIPTION OF THE PREFERRED EMBODIMENTS

In accordance with the present invention, there are generally two preferred embodiments of the inventive covered stent assembly. A first embodiment generally comprises a structural support member, such as a stent, that has first and second opposing wall surfaces thereof that are bounded by metallic or pseudometallic covers. The covers are positioned adjacent the first and second opposing wall surfaces and are either coupled to the structural support member or are coupled to one another through interstitial openings passing through the structural support member. A second embodiment generally comprises at least one metallic or pseudometallic cover that is positioned intermediate two adjacent structural support members, e.g., stents. For purposes of this application, the terms "pseudometal" and "pseudometallic" are intended to mean a biocompatible material which exhibits biological response and material characteristics substantially the same as biocompatible metals. Examples of pseudometallic materials include, for example, composite materials, ceramics, quartz, and borosilicate. Composite materials are composed of a matrix material reinforced with any of a variety of fibers made from ceramics, metals, or polymers. The reinforcing fibers are the primary load carriers of the material, with the matrix component transferring the load from fiber to fiber. Reinforcement of the matrix material may be achieved in a variety of ways. Fibers may be either continuous or discontinuous. Reinforcement may also be in the form of particles. Examples of composite materials include those made of carbon fibers, boron fibers, boron carbide fibers, carbon and graphite fibers, carbon nanotubes, silicon carbide fibers, steel fibers, tungsten fibers, graphite/copper fibers, titanium and silicon carbide/titanium fibers.

The structural support member and the covering member are preferably fabricated entirely of self-supporting films made of biocompatible metals or biocompatible pseudometals. The metal films may either be single layer metal films or plural layer films. The terms "metal film," "thin metallic film" and "metal thin film" are used in this application synonymously to refer to single or plural layer films fabricated of biocompatible metals or biocompatible pseudometals having thicknesses greater than 0 μm and less than about 125 μm.

Figure 1:
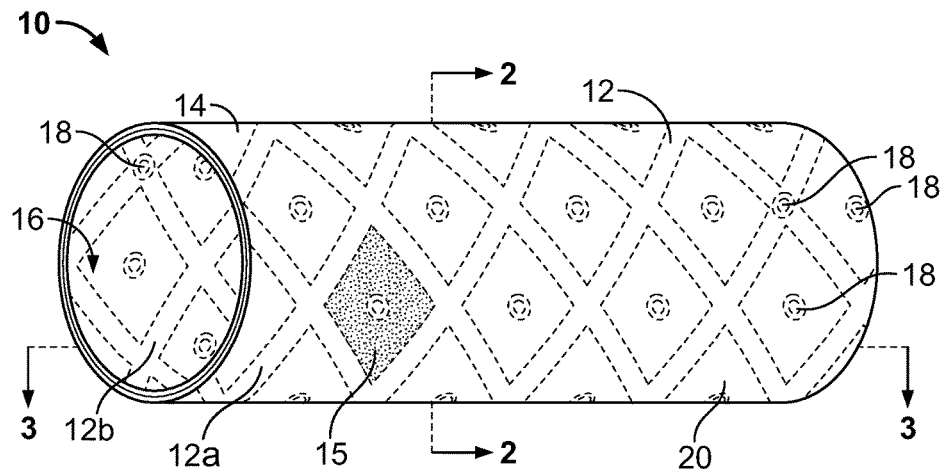
FIG. 1 is a perspective view of a first embodiment of the stent-graft of the present invention.
Figure 2:
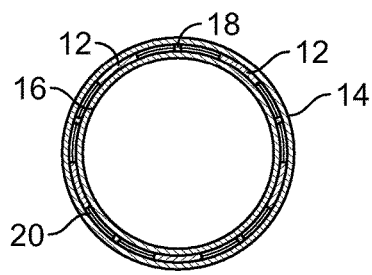
FIG. 2 is a cross-sectional view taken along line 2-2 of FIG. 1.

Turning now to the accompanying figures, FIGS. 1-5 illustrate the first embodiment of the present invention and variations thereof. FIG. 1 illustrates one embodiment of a stent-graft of the present invention. FIG. 2 is a cross-sectional view taken along line 2-2 of FIG. 1, and FIG. 3A is a cross-sectional view taken along line 3-3 of FIG. 1. With particular reference to FIGS. 1 and 2, the inventive stent-graft 10 consists generally of at least one structural support member 12 having a first wall surface 12a and a second wall surface 12b opposing one another, a first cover member 14 and a second cover member 16. The first cover member 14 is positioned adjacent the first wall surface 12a while the second cover member 16 is positioned adjacent the second wall surface 12b of the structural support member 12. The first cover member 14 and the second cover 16 may be coupled either to the structural support member 12 or to one another through interstitial openings 20 passing through the structural support member 12. Coupling of the first cover member 14 and/or the second cover member 16 may be achieved by creating junctions 18 such as by chemical, mechanical or thermal means. For example, the junctions 18 may be formed by welding, adhering using a biocompatible adhesive, or by forming interlocking or interfacing members on opposing surfaces of the support structure 12, the first cover member 14 and/or the second cover member 16 depending upon the surfaces to be coupled. Additionally, junction 18 may be formed by mechanical interference between the support structure 12 and the first cover member 14 and/or the second cover member 16.

Figure 5:
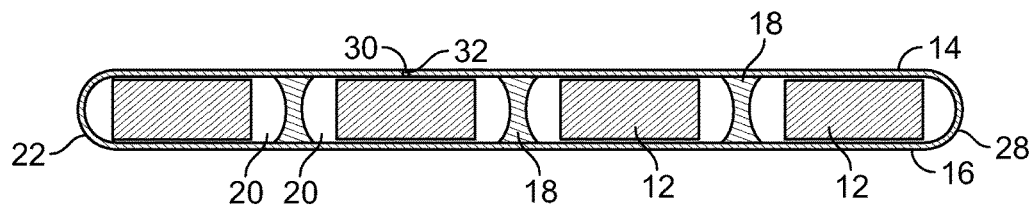
FIG. 5 is a cross-sectional view of a third embodiment of the stent-graft of the present invention.

As illustrated with more particularity with reference to FIGS. 3-5, the first cover member 14 and the second cover member 16 may consist of dual discrete members as depicted in FIGS. 4A, 4B, and 4C. In this version of the first embodiment, each of the first cover member 14 and the second cover member 16 terminate with opposing proximal 24 and distal 26 ends of the respective first cover member 14 and second cover member 16. Junctions 18 may be provided either between the structural support member 12 and the proximal 24 and distal 26 ends of the first 14 and second 16 cover members, between opposing wall surfaces of the first 14 and second 16 cover members and through interstitial spaces in the structural support member 12, or both. Junctions 18 may also be provided between the structural support member 12 and the first 14 and second 16 cover members.

FIG. 4A illustrates an embodiment in which junctions 18 are provided between opposing wall surfaces of the first 14 and second 16 cover members and through interstitial spaces in the structural support member 12. FIG. 4B illustrates an embodiment in which junctions 18 are provided only at the proximal 24 and distal 26 ends of the first 14 and second 16 cover members. FIG. 4C illustrates an embodiment in which junctions 18 are provided directly between the structural support members 12 and the first 14 and second 16 cover members. Thus, the junctions 18 may occur between the cover members 14, 16 and the structural support member 12, between the cover members 14, 16 only, or both.

Figure 3A:
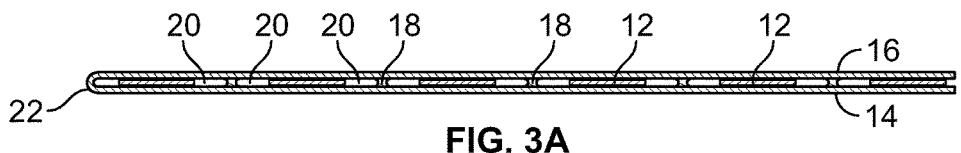
FIG. 3A is a cross-sectional view taken along line 3-3 of FIG. 1.
Figure 3B:
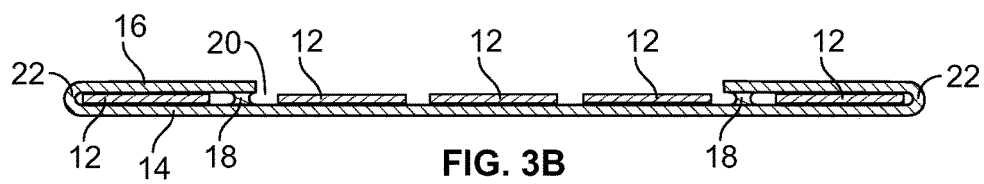
FIG. 3B is a cross-sectional view of a variation of a first embodiment of the stent-graft of the present invention.
Figure 3C:
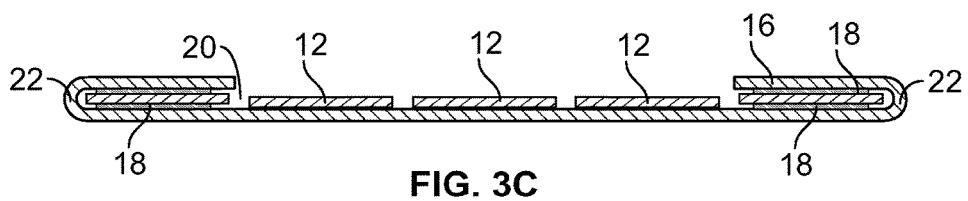
FIG. 3C is a cross-sectional view of another variation of a first embodiment of the stent-graft of the present invention.

Alternatively, as depicted in FIGS. 3A, 3B, and 3C, the first cover member 14 and the second cover member 16 may comprise of a single cover member that is positioned adjacent both the first and second wall surfaces of the structural support member 12 and has an eversion region 22 positioned at either a proximal or distal end of the structural support member, or at both the proximal and distal ends of the structural support member 12. Alternatively, dual cover members may be employed with a junction between the first cover member 14 and the second cover member 16 being formed therebetween at the eversion region 22.

FIG. 3A illustrates an embodiment in which the first cover member 14 and the second cover member 16 comprise of a single cover member that is positioned adjacent both the first and second wall surfaces of the structural support member 12 and has an eversion region 22 positioned at either a proximal or distal end of the structural support member. FIG. 3B illustrates an embodiment in which the first cover member 14 and the second cover member 16 comprise of a single cover member that is positioned adjacent at least a portion of both the first and second wall surfaces of the structural support member 12 and has an eversion region 22 positioned at both the proximal and distal end of the structural support member 12. FIG. 3B also illustrates an embodiment in which junctions 18 are provided between opposing wall surfaces of the first 14 and second 16 cover members and through interstitial spaces in the structural support member 12. FIG. 3C illustrates an embodiment in which the first cover member 14 and the second cover member 16 comprise of a single cover member that is positioned adjacent at least a portion of both the first and second wall surfaces of the structural support member 12 and has an eversion region 22 positioned at both the proximal and distal end of the structural support member 12. FIG. 3C also illustrates an embodiment in which junctions 18 are provided directly between the structural support members 12 and the first 14 and second 16 cover members.

In accordance with yet another variation of the first embodiment of the invention illustrated in FIG. 5, the first cover member 14 and the second cover member 16 may consist of a single cover member 14 that is everted over both the distal end 22 of the structural support member 12 and over the proximal end 28 of the structural support member 12, thereby forming distal and proximal eversion regions 22, 28, and opposing ends 30, 32 of the first cover member 14 are either conjoined to one another, coupled to the structural support member 12 or joined at a junction region 18 to an opposing surface of the first cover member 14.

Figure 6:
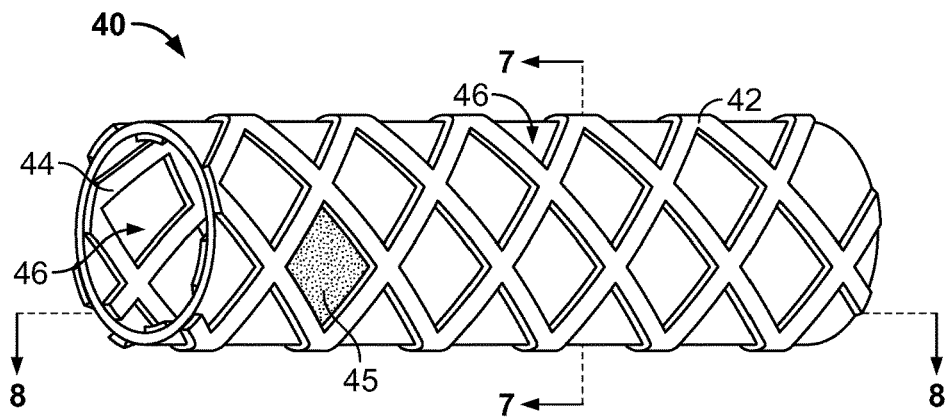
FIG. 6 is a perspective view of a fourth embodiment of the stent-graft of the present invention.

Each of the first 14 and second 16 cover members preferably has a plurality of openings 15 passing there through. In FIGS. 1 and 6, the plurality of openings 15 and 45, respectively, are shown in one region of the first 14 and second 16 cover members and the metallic cover member 46 for illustrative purposes only. It is contemplated that the plurality of openings 15 and 45 may be present throughout the first 14 and second 16 cover members and the metallic cover member 46 or may be in present in various areas of the first 14 and second 16 cover members and the metallic cover member 46. Each of the plurality of openings 15 preferably has a pore size within the range of about 0.1 μm to about 1000 μm in at least one of an x or y-axis of the opening, with the total open surface area of the first 14 and second 16 cover being between 0.001 to 90% and which permit cellular and sub-cellular physiological matter, such as proteins, to pass through the openings 15 without permitting fluid seepage there through. As used herein, the term "pore size" is intended to connote a dimension in at least one of an x-axis or a y-axis of the opening 15. The total open surface area of the first 14 or second 16 cover may be calculated by dividing the surface area of each the plurality of openings 15 by the total surface area on either the luminal or abluminal surface of the first 14 or second 16 cover member. The plurality of openings 15 also impart dimensional flexibility to the first 14 and second 16 cover members and permits flexibility, compressibility and expandability along the longitudinal axis of the stent-graft device 10, while also permitting compliance, foldabilty and expandability in the radial axis of the stent-graft device 10. The plurality of openings 15 are preferably provided in a pattern array in order to maximize the physical properties of the first 14 and second 16 cover members and, hence, the resulting inventive stent-graft 10. For example, the pattern array may be provided to selectively enhance longitudinal flexibility while reinforcing against radial compliance.

Figure 7:
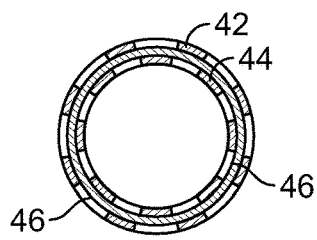
FIG. 7 is a cross-sectional view taken along line 7-7 of FIG. 6.
Figure 8:
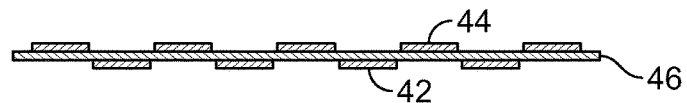
FIG. 8 is a cross-sectional view taken along line 8-8 of FIG. 6.

A second embodiment of the inventive stent-graft 40 is illustrated with reference to FIGS. 6-10. FIG. 6 is a perspective view of one embodiment of the stent-graft of the present invention. FIG. 7 is a cross-sectional view taken along line 7-7 of FIG. 6, and FIG. 8 is a cross-sectional view taken along line 8-8 of FIG. 6. Stent-graft 40 consists generally of at least a first structural support member 42 and a second structural support member 44, which are, for example, tubular stent members, and a metallic cover member 46 having a plurality of openings 45. The at least two structural support members 42, 44, for ease of reference, will be referred to as stent members 42, 44. Stent members 42, 44 are preferably generally tubular in configuration, and may be formed as tubular members or initially as planar members that are rolled into a tubular configuration. Alternatively, where it is desirable that the first and second structural support members 42, 44 not constitute stents, the first and second structural support members 42, 44 may be configured to define alternative geometries suitable for a particular application. Such alternative geometries may include, for example, planar geometries for use as patches, frustroconical geometries such as for use as anchors for dental implants or other complex geometries such as for osteal implants.

Where the first structural support member 42 and the second structural support member 44 are selected as stents, the stent members 42, 44 are preferably positioned concentrically relative to one another. The metallic cover member 46 is then positioned concentrically intermediate the first and second stent members 42, 44 along at least a portion of a longitudinal axis of the first and second stent members 42, 44. The first 42 and second 44 structural support members may either be joined, as described above, to the metallic cover member 46 or may be joined to one another outside the surface area of the metallic cover member 46.

Figure 9:
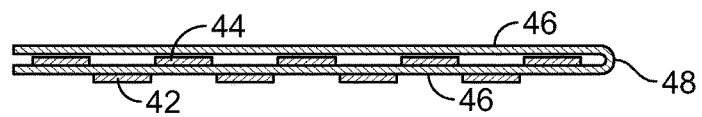
FIG. 9 is a cross-sectional view of a fifth embodiment of the stent-graft of the present invention.
Figures 10, 11:
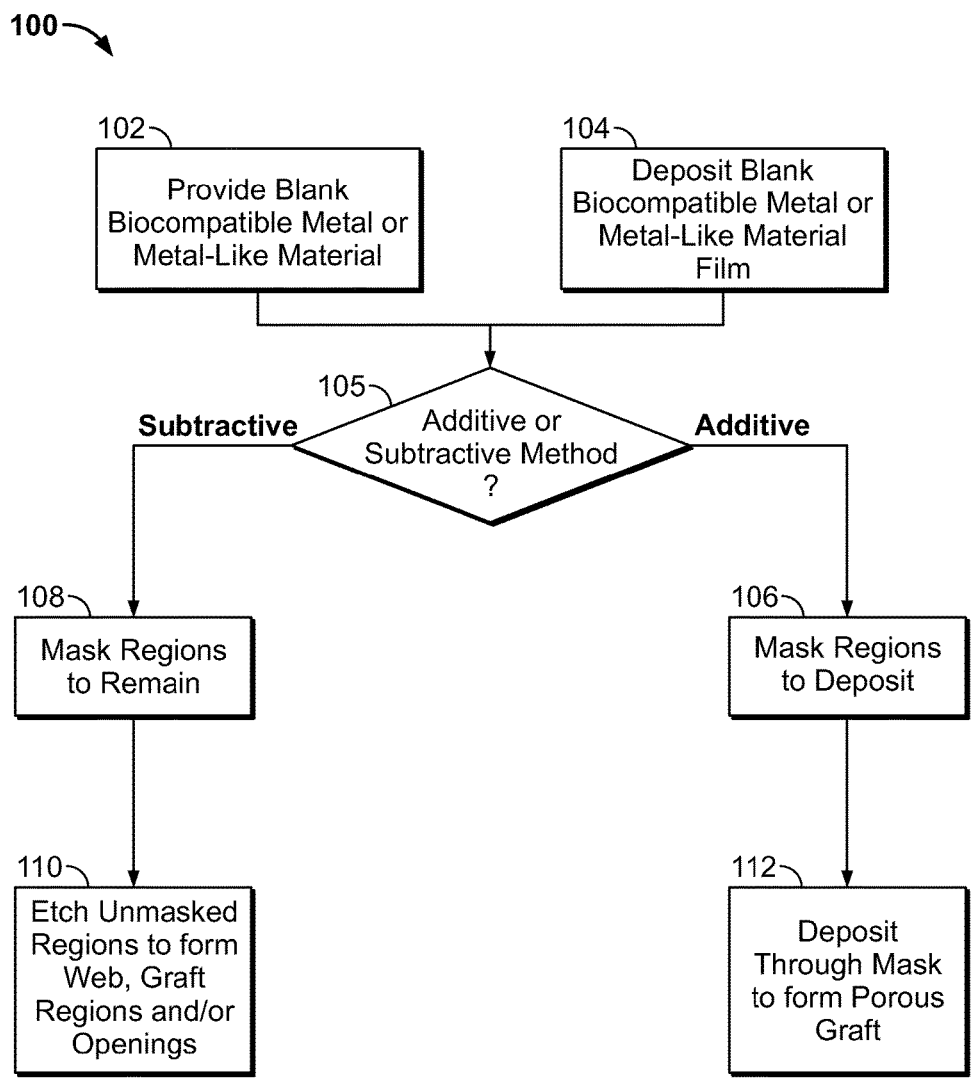
FIG. 10 is a cross-sectional view of a sixth embodiment of the stent-graft of the present invention.
FIG. 11 is a flow diagram illustrating fabrication methodologies for making the inventive stent-graft of the present invention.

As depicted in FIGS. 9 and 10, a multilayered construction may be formed by extending the metallic cover member 46 and everting the metallic cover member 46 over one or both of the proximal 52 and/or distal 54 ends of the stent-graft. The eversion regions 48, 50 may be positioned at the proximal 52 or distal 54 ends of the metallic cover member 46, or both.

A plurality of openings 45 is provided and passes through the thickness of the cover member 46. As with the first embodiment of the invention, each of the plurality of openings 45 preferably has an pore size within the range of 0.1 μm to 1000 μm, with the total open surface area of the graft being between 0.001 to 90% and which permit cellular and sub-cellular physiological matter, such as proteins, to pass through the openings 45 without permitting fluid seepage there through. Both the pore size of the openings 45 and the total open area of the cover member 46 may be selected in view of the following non-exclusive factors: the desired flexibility of the cover member 46, the desired hoop strength of the cover member 46, the desired degree of geometric enlargement due to deformation of the openings 45 and the desired delivery profile size.

The inventive cover member 46 may be fabricated of pre-existing conventionally produced wrought materials, such as stainless steel or nitinol hypotubes, or may be fabricated by thin film vacuum deposition techniques. In addition to wrought materials that are made of a single metal or metal alloy, the inventive grafts may be comprised of a monolayer of biocompatible material or of a plurality of layers of biocompatible materials formed upon one another into a self-supporting laminate structure. Laminate structures are generally known to increase the mechanical strength of sheet materials, such as wood or paper products. Laminates are used in the field of thin film fabrication also to increase the mechanical properties of the thin film, specifically hardness and toughness. Laminate metal foils have not been used or developed because the standard metal forming technologies, such as rolling and extrusion, for example, do not readily lend themselves to producing laminate structures. Vacuum deposition technologies can be developed to yield laminate metal structures with improved mechanical properties. In addition, laminate structures can be designed to provide special qualities by including layers that have special properties such as superelasticity, shape memory, radio-opacity, corrosion resistance etc.

According to the preferred method of making the graft of the present invention, the graft is fabricated of vacuum deposited metallic and/or pseudometallic films. With particular reference to FIG. 11, the fabrication method 100 of the present invention is illustrated. A precursor blank of a conventionally fabricated biocompatible metal or pseudometallic material may be employed at step 102. Alternatively, a precursor blank of a vacuum deposited metal or pseudometallic film may be employed at step 104. A decision 105 is made whether to process the precursor blank from step 102 or step 104 by either subtractive or additive processing is made. If a subtractive process is to be employed, the precursor blank material obtained either from step 102 or step 104 may then be masked at step 108 leaving exposed only those regions which will define a plurality of openings and which will be removed to form the openings. The exposed regions from step 108 are then subjected to removal at step 110, either by etching, such as by wet or dry chemical etching processing, with the etchant being selected based upon the material of the precursor blank, or by machining, such as by laser ablation or EDM. Alternatively, when employing the vacuum deposition step 104, a pattern mask corresponding to the plurality of openings to be formed later and with openings to permit deposition of the graft material through the mask, may be interposed at step 106 between the target and the source and the metal or pseudometal deposited at step 112 through the pattern mask to form the graft material with openings corresponding to the masked regions. Further, when employing the vacuum deposition step 104, plural film layers maybe deposited to form a laminate film structure of the film prior to or concurrently with forming the plurality of openings.

Where a laminate film is fabricated as the graft, it is necessary to provide for good adhesion between the layers. This may be achieved by providing for a relatively broad interfacial region rather than for an abrupt interface. The width of the interface region may be defined as the range within which extensive thermodynamic parameters change. This range can depend on the interface area considered and it may mean the extent of interface microroughness. In other words, adhesion may be promoted by increased interfacial microroughness between adjacent layers within the film. The microroughness may be imparted by chemical or mechanical means, such as chemical etching or laser ablation, or may be included as a process step during vacuum deposition by selectively depositing a metal or pseudometallic species to form the microroughness.

Thus, the present invention provides a new metallic and/or pseudometallic implantable graft that is biocompatible, geometrically changeable either by folding and unfolding or by application of a plastically deforming force, and capable of endoluminal delivery with a suitably small delivery profile. Suitable metal materials to fabricate the inventive covers are chosen for their biocompatibility, mechanical properties, i.e., tensile strength, yield strength, and their ease of deposition include, without limitation, the following: titanium, vanadium, aluminum, nickel, tantalum, zirconium, chromium, silver, gold, silicon, magnesium, niobium, scandium, platinum, cobalt, palladium, manganese, molybdenum and alloys thereof, such as chromium-cobalt alloy, zirconium-titanium-tantalum alloys, nickel-titanium, and stainless steel. Examples of pseudometallic materials potentially useful with the present invention include, for example, composite materials, ceramics, quartz, and borosilicate.

The present invention also provides a method of making the inventive stent-graft devices by vacuum deposition of a graft-forming metal or pseudometal and formation of the openings either by removing sections of deposited material, such as by etching, EDM, ablation, or other similar methods, or by interposing a pattern mask, corresponding to the openings, between the target and the source during deposition processing. Alternatively, a pre-existing metal and/or pseudometallic film manufactured by conventional non-vacuum deposition methodologies, such as wrought hypotube, may be obtained, and the openings formed in the pre-existing metal and/or pseudometallic film by removing sections of the film, such as by etching, EDM, ablation, or other similar methods. An advantage of employing laminated film structures to form the inventive graft is that differential functionalities may be imparted in the discrete layers. For example, a radiopaque material such as tantalum may form one layer of a structure while other layers are chosen to provide the graft with its desired mechanical and structural properties.

While the present invention has been described with reference to its preferred embodiments, those of ordinary skill in the art will understand and appreciate that variations in materials, dimensions, geometries, and fabrication methods may be or become known in the art, yet still remain within the scope of the present invention which is limited only by the claims appended hereto.

What is claimed is:

1. A tubular medical device having an inner luminal surface and outer abluminal surface, comprising:
   a) a structural support member having first and second wall surfaces thereof, the structural support member having at least one open space passing through the first and second wall surfaces, and being comprised of at least one of a metallic and pseudometallic laminate material; and
   b) at least one tubular cover member consisting of a coherent laminate film of at least one of a metallic and pseudometallic material, the at least one tubular cover member being positioned adjacent against at least a portion of both the luminal and abluminal surfaces of the medical device and covering the at least one open space of the structural support member.

2. The tubular medical device according to claim 1, wherein the laminate is selected from the group consisting of titanium, vanadium, aluminum, nickel, tantalum, zirconium, chromium, silver, gold, silicon, magnesium, niobium, scandium, platinum, cobalt, palladium, manganese, molybdenum and alloys thereof, chromium-cobalt alloy, zirconium-titanium-tantalum alloy, nickel-titanium alloy, and stainless steel.

3. The tubular medical device according to claim 1, wherein the at least one metallic and pseudometallic laminate further comprises a pseudometallic material selected from the group consisting of ceramic, quartz, borosilicate, carbon fibers, boron fibers, boron carbide fibers, carbon nanotubes, carbon and graphite fibers, silicon carbide fibers, steel fibers, tungsten fibers, graphite/copper fibers, titanium fibers, and silicon carbide/titanium fibers.

4. The tubular medical device according to claim 1, wherein the at least one tubular cover member further comprises a plurality of openings passing through the tubular cover member.

5. The tubular medical device according to claim 4, wherein each of the plurality of openings has a pore size between about 0.1 μm to about 1000 μm in either an x-axis or a y-axis of the opening.

6. The tubular medical device according to claim 4, wherein the plurality of openings form a total open surface area in the tubular cover member between about 0.001 to about 90% of the area of one of a first or a second surface of the tubular cover member.

7. The tubular medical device according to claim 1, wherein the at least one tubular cover member is coupled to at least one of a proximal and distal end of the structural support member.

8. The tubular medical device according to claim 1, wherein the at least one tubular cover member and a second tubular cover member are coupled to each other through the at least one open space of the structural support member.

9. The tubular medical device according to claim 1, further comprising at least one affixation junction between the at least one tubular cover member and the structural support member or the at least one tubular cover member.

10. The tubular medical device according to claim 9, wherein the at least one affixation junction is selected from the group consisting a chemical, mechanical and thermal affixation junction.

11. The tubular medical device according to claim 10, wherein the mechanical affixation junction further comprises an interference fit.

12. The tubular medical device according to claim 10, wherein the mechanical affixation junction further comprises an interfacing detent and trough.

13. The tubular medical device according to claim 7, wherein the at least one tubular cover member is coupled to the at least one of a proximal and distal end of the structural support member by at least one of a chemical, thermal or mechanical junction.

14. The tubular medical device according to claim 8, wherein the first and second tubular cover members are attached to one another by at least one of a chemical, thermal and mechanical junction.

15. The tubular medical device according to claim 8, wherein the open space is capable of geometric deformation about the attachment between the first and second tubular cover members.

16. The tubular medical device according to claim 1, further comprising a defined junction region on each of the structural support member and the at least one tubular cover member in alignment with one another and a junction formed therebetween.

17. A covered stent device, comprising:
a) a diametrically expandable stent having a luminal and an abluminal wall surface and a wall thickness therebetween, and at least one open space passing through the luminal and abluminal wall surfaces; and
b) at least one tubular cover member consisting of a thin metallic laminate film having a plurality of openings passing therethrough, and positioned concentrically adjacent to and covering an entire circumferential aspect of the diametrically expandable stent and covering the at least one open space of the diametrically expandable stent and the at least one tubular cover member being radially-expandable, wherein each of the plurality of openings are smaller than the at least one open space of the diametrically expandable stent.

18. The covered stent device, according to claim 17, wherein the thin metallic laminate film is selected from the group consisting of titanium, vanadium, aluminum, nickel, tantalum, zirconium, chromium, silver, gold, silicon, magnesium, niobium, scandium, platinum, cobalt, palladium, manganese, molybdenum and alloys thereof, such as chromium-cobalt alloy, zirconium-titanium-tantalum alloys, nickel-titanium alloy, and stainless steel.

19. The covered stent device according to claim 17, wherein at least a portion of the at least one tubular cover member is concentrically carried adjacent each of the luminal and abluminal wall surfaces of the diametrically expandable stent, wherein the portion of the at least one tubular cover member adjacent the luminal wall surface is coupled to the portion of the at least one tubular cover member adjacent the abluminal wall surface through the at least one open space of the diametrically expandable stent in such a manner as to permit geometric deformation of the at least one open space.

20. The covered stent device according to claim 17, wherein the at least one tubular cover member is coupled to at least one of a proximal and a distal end of the diametrically expandable stent.

21. The covered stent device according to claim 19, wherein the coupling further comprises at least one of a chemical, thermal or mechanical junction.

22. The covered stent device according to claim 20, wherein the coupling further comprises at least one of a chemical, thermal or mechanical junction.

23. The covered stent according to claim 21, wherein each of the plurality of openings of the at least one tubular cover member has a pore size between about 0.01 μm to about 1000 μm.

24. The covered stent according to claim 17, wherein the plurality of openings of the at least one tubular cover member form a total open surface area of the tubular cover member between about 0.001 to about 90% of the area of one of an abluminal or luminal surface of the tubular cover member.

25. The covered stent device according to claim 17, further comprising a polymeric material capable of releasing a pharmacologically active agent therefrom disposed on at least one of the diametrically expandable stent or the at least one tubular cover member, whereby the polymeric material does not subtend the openings in the at least one tubular cover member or the at least one open space of the diametrically expandable stent.

26. A medical device, comprising:
a) A body member consisting of a metallic or pseudometallic laminate film having a first and a second wall surface and thereof;
b) at least two structural support members, the first structural support member being positioned concentrically adjacent the first wall surface of the body member and the second structural support member being positioned concentrically adjacent the second wall surface of the body member, wherein the body member is bound between the first and second structural members is bound between the first and second structural members; and
c) wherein the structural support members each comprise a stent having a first wall surface, a second wall surface, and at least one open space passing through the first and second wall surfaces, the at least one open space subtended by a wall surface of the body member.

27. The medical device according to claim 26, wherein the metallic or pseudometallic laminate film is selected from the group consisting of titanium, vanadium, aluminum, nickel, tantalum, zirconium, chromium, silver, gold, silicon, magnesium, niobium, scandium, platinum, cobalt, palladium, manganese, molybdenum and alloys thereof, chromium-cobalt alloy, zirconium-titanium-tantalum alloy, nickel-titanium alloy, and stainless steel.

28. The medical device according to claim 26, wherein the laminate film comprised of at least one of a metallic and pseudometallic material further comprises a thin film laminate comprised of a pseudometallic material selected from the group consisting of ceramic, quartz, borosilicate, carbon fibers, boron fibers, boron carbide fibers, carbon and graphite fibers, carbon nanotubes, silicon carbide fibers, steel fibers, tungsten fibers, graphite/copper fibers, titanium fibers, and silicon carbide/titanium fibers.

29. The medical device according to claim 26, wherein the body member further comprises a plurality of openings passing through the first and second wall surfaces of the body member.

30. The medical device according to claim 26, wherein at least one of the two structural support members is coupled to the body member at least at one of a proximal and distal end of the body member.

31. The medical device according to claim 29, wherein each of the plurality of openings of the body member has a dimension between about 0.1 μm to 1000 μm in either of an x-axis or y-axis of the opening.

32. The medical device according to claim 29, wherein the plurality of openings of the body member form a total open surface area in the body member between about 0.001 to about 90% of the surface area of the body member.

33. The medical device according to claim 26, wherein the body member has a thickness between about 0.3 μm and 125 μm.

* * * * *